United States Patent
Horstmann et al.

(10) Patent No.: US 9,506,742 B2
(45) Date of Patent: Nov. 29, 2016

(54) METHOD FOR PHOTOACOUSTIC TOMOGRAPY

(71) Applicant: Medizinisches Laserzentrum Lubeck GmbH, Lubeck (DE)

(72) Inventors: Jens Horstmann, Lubeck (DE); Ralf Brinkmann, Lubeck (DE)

(73) Assignee: Medizinisches Laserzentrum Lubeck GmbH (DE)

( * ) Notice: Subject to any disclaimer, the term of this patent is extended or adjusted under 35 U.S.C. 154(b) by 0 days.

(21) Appl. No.: 14/195,059

(22) Filed: Mar. 3, 2014

(65) Prior Publication Data

US 2014/0247456 A1 Sep. 4, 2014

(30) Foreign Application Priority Data

Mar. 4, 2013 (EP) .................. 13157616

(51) Int. Cl.
*G01B 9/02* (2006.01)
*A61B 5/00* (2006.01)

(52) U.S. Cl.
CPC ......... *G01B 9/02095* (2013.01); *A61B 5/0073* (2013.01); *A61B 5/0095* (2013.01)

(58) Field of Classification Search
CPC .......... G01B 9/02094; G01B 9/02095; G01B 9/02096; G01B 11/162
USPC ............................................ 356/502, 511
See application file for complete search history.

(56) References Cited

U.S. PATENT DOCUMENTS

| | | | |
|---|---|---|---|
| 2012/0200845 A1* | 8/2012 | Rousseau et al. | 356/72 |
| 2012/0320368 A1* | 12/2012 | Jiao et al. | 356/72 |
| 2014/0185055 A1* | 7/2014 | Wang | 356/479 |

OTHER PUBLICATIONS

Pendrini et al., Double pulse electronic speckle interferometry, 1993, Journal of Modern Optics, vol. 40, No. 1, 89-96.*
European Search Report prepared by European Patent Office on Aug. 2, 2013, for European Application No. 13157616.7.
Lin et al.: "Study of photoacoustic imaging based on all-optical detection", Proceedings of SPIE, vol. 7160; Dec. 3, 2008.
Kemper et al.: "Endoscopic Double-Pulse Electronic-Speckle-Pattern Interferometer for Technical and Medical Intracavity Inspection", Applied Optics, vol. 39, No. 22; Aug. 1, 2001.
Trillo et al.: "Numerical reconstruction of acoustic bulk waves in aluminium from TV holography surface displacement measurements", Proceedings of SPIE, vol. 7098; Jun. 4, 2008.
Pedrini et al., "Double pulse-electronic speckle interferometry," Journal of Modern Optics, 1993, vol. 40(1), pp. 89-96.
Carp et al., "Optoacoustic imaging based on the interferometric measurement of surface displacement," Journal of Biomedical Optics, 2007, vol. 12(6), pp. 064001-1-064001-9.

\* cited by examiner

*Primary Examiner* — Jonathan Hansen
(74) *Attorney, Agent, or Firm* — Sheridan Ross P.C.

(57) ABSTRACT

The invention relates to a method for photoacoustic tomography of a sample, deformations on a measurement surface of the sample being measured as a function of location and time, the deformations resulting from the absorption of a pulsed excitation radiation on at least one spectrally addressable target structure in the sample interior while emitting thermomechanical pressure waves in the direction of the measurement surface, and the measured deformations being fed to a reconstruction method for determining the position of the target structure in the sample interior.

11 Claims, 2 Drawing Sheets

METHOD FOR PHOTOACOUSTIC TOMOGRAPY

This application claims the benefit of European Patent Application No. 13157616.7 filed on Mar. 4, 2013, the entire contents of which is incorporated herein by reference.

The invention relates to a method for Photoacoustic Tomography of sample volumes that exhibit, in their interior, spectrally addressable absorption contrasts for electromagnetic radiation for at least one target structure. The invention also relates to an apparatus for photoacoustically localizing physiological structures inside a biological tissue.

In Photoacoustic Tomography (PAT), a sample volume is irradiated with excitation light from a predetermined part spectrum of the electromagnetic spectrum. The excitation light is to enter into the sample interior and possibly be scattered in the process, but absorbed only weakly or not at all by the predominant part of the sample material. On the other hand, predetermined target structures present in the sample interior in an a priori unknown distribution are to absorb the excitation light while heating up and thus effect a localized thermal expansion of the absorber and, in the boundary area, also of the surrounding sample material.

The predetermined part spectrum of the excitation radiation is a function of the material properties of the sample and in particular also of those of the target structures that are to be localized photoacoustically. The user himself will have to chose a suitable part spectrum for his specific sample in the individual case. Per definition, a sample volume that exhibits "spectrally addressable" absorption contrasts for a target structure on the inside is to be such a one for which a part spectrum of the electromagnetic spectrum can be found from which light is absorbed differently by the target structure than by the surroundings of the target structure.

In principle, the PAT can also be used for localizing target structures that absorb the light worse than their surroundings and thus measurably interfere with the spreading of pressure waves in the material, for example trapped air in the material or other material defects (defect screening).

In PAT, the absorptive power for the excitation radiation is commonly higher in a target structure than in the surroundings of the target structure. For improved comprehension, it is only this situation that will be discussed below, the transferability to defect screening having to be regarded as prior art.

If the sample is irradiated with the excitation light in a pulsed manner, pressure waves that are limited in time are triggered inside the sample (photoacoustic effect). The pressure waves that are generated inside by absorption and then propagate to the sample surface lead to small and short-term deformations of the sample surface.

However, this presupposes that the pulse energy of the excitation light exhibits an appropriate value that likewise has to be selected by the user himself for his specific sample. If the pulse energy is too low, the energy that has been input dissipates during the pressure-wave propagation so that in practice no deformations can be detected. In contrast, pulse energy that is too high can irreversibly damage the sample.

If the pulse duration of an excitation-light pulse is in the order of magnitude of a few nanoseconds, preferably in the range of the acoustic confinement time of the absorber, and the irradiation in the range of a few $mJ/cm^2$, then deformation amplitudes in the order of magnitude of a few nanometers have to be expected at the sample surface over a time span of microseconds.

Detection of deformations of the sample surface and the subsequent evaluation of their spatial and temporal behavior permit the target structures inside the sample to be localized and even qualified and quantified.

In the paper by Carp and Venugopalan, "Optoacoustic imaging based on the interferometric measurement of surface displacement", Journal of Biomedical Optics, Vol. 12(6), 2007, p. 064001 ff., it is for example explained how the source distribution of the pressure waves is reconstructed voxel by voxel from the temporary and locally resolved deformation data when the speed of sound of the sample is known (see there FIG. 3 and text). Such reconstruction methods based on "back projection" are widely used in computed tomography (CT) or digital tomosynthesis (DT). Commonly, these are computationally intensive methods that are not carried out until after termination of the complete measurement-data acquisition.

It is assumed below that reconstructing the source distribution of the optically excited pressure waves is a problem that is solved per se. PAT can be carried out in principle as soon as deformations of the sample surface can be detected with sufficient precision and with sufficient temporal resolution.

Carp and Venugopalan for example describe a measurement of pressure oscillations generated using a pulsed excitation laser beam. The measurement setup is based there on a Mach Zehnder Interferometer that uses an He—Ne laser as observation light source. The observation laser light is reflected dichroically into the beam path of the excitation laser and scattered primarily from the sample surface. The interferometer detects shifts of the sample surface from the phase shift of the observation laser light relative to a predetermined reference oscillation that is introduced by a controllable acousto-optic modulator.

It is particularly desirable to carry out the pressure-wave detection in a none-contacting manner simply by illumination, imaging and temporal observation of the sample surface and to dispense with any arrangement of pressure transducers on the sample. Pressure transducers can, on the one hand, shield the sample against the excitation radiation and, on the other hand, require acoustic impedance matching to the sample material.

Carp and Venugopalan apply the observation laser light locally in contrast to the excitation light that is applied in a two dimensional fashion. Local interference phases and thus surface shifts can be determined, it then being possible to record a complete time series of signals at each measuring point. To determine the spatial distribution of the surface deformations of the sample it is necessary to shift the measurement point irradiated with observation light relative to the sample which is done here for example using a sample holder that can be moved at right angles to the irradiation direction. Such shifts each require a measurement break of approximately 0.5 s, to which another 0.3 to 0.5 s measurement time is added for each measurement point for 350 to 750 measurement points until a sample surface of a few square centimeters has been scanned. The authors specify an acquisition duration of 7 to 15 minutes for all data requisite for tomographic reconstruction.

Data acquisition lasting several minutes is disadvantageous for applications where the sample cannot be firmly clamped in a vibration-proof holder. If, however, the sample is even living tissue, then unavoidable proper motion of the sample has to be taken into account that will interfere with the measurement result or even render it completely useless. In addition, general heating up of the sample by the repeated irradiation with excitation light can be assumed, leading to the expansion of the sample during the measurement time.

A possibility for shortening the measurement time can be seen in that the location-dependent deformation of the sample surface as a function of time is detected simultaneously at as many locations as possible. The totality of the deformation measurement values of a measurement surface on the sample surface at a specific point in time is to be designated as deformation profile below. A temporal sequence of deformation profiles having a sufficiently high density of supporting points with respect to time and 2D local coordinates (of the measurement surface) is a suitable starting data set for tomographic reconstruction. To obtain the data set, it can be considered to use a measurement setup having a digital camera and a holographic method from elastometry.

In a theoretical paper, Lin et al. ("Study of photoacoustic imaging based on all-optical detection", Proceedings of SPIE, Vol. 7160, 2008, p. 71602K-1) describe an ESPI based design for detecting transient surface deformations that are excited in a phantom by means of pressure waves from an absorber irradiated by a laser pulse. According to this, the detected surface deformations become usable, as is common for PAT, for reconstructing the position of the absorber using algorithms not described by Lin in more detail.

However, according to Lin's idea, in each case only one pulse is to be used for excitation and detection, the detection pulse being supposed to be repeatedly shiftable in time. Using this described method, only measurements of quiescent objects that do not change are possible. Slightest motion between two excitation pulses e.g. by blood flowing, breathing, or temperature drift—even by only a few micrometers, typical for living objects—makes it impossible to use the described method to consecutively detect a topography that continuously changes with time.

The term "double-pulse electronic speckle interferometry (DP ESPI)" is of great importance below for the present invention. It is clarified below how it is to be understood in the context of the present application.

In a very general sense DP ESPI is a method for detecting transient vibrations of a surface where two temporary consecutively carried-out illumination procedures of the surface using coherent light and recording in each case at least one speckle pattern produced by scattering light during one illumination procedure take place on a two-dimensional light-detector array (electronic camera having light-sensitive pixels below). In the case of a sufficiently short temporal distance of the illumination procedures and only very little deformation, the individual speckles of the at least two speckle images are almost unchanged with the exception of their phases that are highly sensitive to the distance of the individual areas of the scattering surface from the camera. In DP ESPI in principle the phase difference of the speckles is determined between the two illumination moments, and the local movement of the surface having taken place in the meantime is deduced from this.

A possible embodiment of DP ESPI is known from the paper by Pedrini et al. "Double-pulse electronic speckle interferometry", JOURNAL OF MODERN OPTICS, 1993, VOL. 40, No. 1, 89-96. This paper reports the measurement of the deformations of a metal plate that is excited to oscillate by pendulum impact. Here, the plate surface is illuminated using observation laser light and imaged onto a CCD camera. A small fraction (10%) of the observation light is reflected out as reference beam prior to the sample. A fraction of the remaining observation light is scattered by the sample and guided as sample beam through an aperture to the CCD camera. The purpose of the aperture is to increase the mean size of the speckles present in the sample beam approximately to the fourfold width of the camera pixel. At the same time, the reference beam impinges on the camera plane at an angle relative to the sample beam so as to arrange a phase ramp—and at the same time also a fringe pattern having the interference-light intensity—along the pixel arrangement (see there FIG. 4). If the period length of the fringe pattern is smaller than the mean speckle diameter and at the same time has a size of at least three (here: four) camera pixel distances, then a phase profile can be directly calculated from two speckle patterns recorded at a short interval one after the other, the profile showing the deformation of the sample between the two illumination pulses. A deformation profile results therefrom by means of "phase unwrapping" (see there FIG. 5, in particular FIG. 5e).

In principle, the introduction of the interference angle between the reference beam and the object beam can be dispensed with if the geometric path of the reference beam relative to the object beam can be altered in a defined manner in the sub-wavelength range, for example by moving mirrors. In this case, for determining a phase profile it is necessary to sequentially record at least three images having differing phase positions. This is known as ESPI variant "Temporal Phase Shifting" which however, is suitable for time-critical processes only to a limited extent due to the fact that the mirrors cannot be driven at any arbitrarily high speed.

An alternative solution to this consists in using at least three light-sensitive sensors instead of one. The light that includes the optical phase as a result of interference between object beam and reference beam, has to be imaged, according to the ESPI principle, having at least three known phase positions between the two beams. If the light is distributed using several beam splitters to at least three sensors that can be finely adjusted geometrically according to the required phase position or are already appropriately constructed, the three interference images can be recorded simultaneously. In this manner, the method can be employed also for time-critical processes and is in principle equivalent to the approach described above using a phase ramp.

It is also possible to use a color camera, therefore a sensor having a pixel arrangement that is dependent on the spectrum. Different color filters are arranged here in front of the mutually neighboring pixels in a periodic repetition. At least three different wavelengths are simultaneously used for illuminating the sample, only part of the camera pixels then being sensitive for the wavelengths. The modification of the optical path length is for example to be realized by means of dichroic elements in the beam path.

In this sense, further, in principle equivalent, modifications are conceivable. A structured phase mask in front of the sensor can for example modify, in a manner defined for each pixel, the optical path length.

The DP ESPI principle is often determined for detecting the change in the topography of a surface by two measurement pulses applied shortly one after the other.

Kemper et al. ("Endoscopic Double-Pulse Electronic-Speckle-Pattern Interferometer for Technical and Medical Intra-Cavity Inspection", APPLIED OPTICS, Vol. 39, No. 22, 2000, p. 3899) suggest using the method for endoscopic application to determine tactile equivalents for the operator. However, a consistent temporal sequence of the change in topography as required for PAT is not possible in this way.

Trillo et al. ("Numerical reconstruction of acoustic bulk waves in aluminium from TV holography surface displacement measurements" Proceedings of SPIE, Vol. 7098, 2008, p. 70980G-1) suggest a method for materials testing that optically scans ultrasound waves injected on an object side, after passage through the object, on the opposite detection side. By analyzing the measured acoustic wavefronts, sound-scattering or absorbing materials defects can be inferred. Use of this method in biological structures corresponds to a type of ultrasound imaging, having the known limitations regarding contrast and resolution and therefore cannot be compared to photo-acoustic methods.

Despite that fact that on the one hand ESPI and in particular DP ESPI have been known since the late 1970s and on the other hand repeating 2D images using time delay and gating methods have been used for many decades to analyze fast processes involving large changes in surface, it appears that so far no method has been suggested for non-contacting, in particular optical, detection of topographic changes in the nanometer range—as is the case with PAT—that could also be utilized with objects that move as a whole relative to the camera and/or change intrinsically.

A problem can here be seen in that excitation of pressure waves in PAT takes place "at some time" and "at some place" in the sample and it is thus not clear how the deformation profiles that can be determined using DP ESPI can be put into a temporal reference frame suitable for PAT reconstruction. Furthermore, in the case of biological tissues the surface is not clearly defined in terms of speckle production since the observation light penetrates the sample and the speckles can thus be assigned a volume scattering and speckle shifting is based on changes in this volume close to the surface. This makes back transformation to the localization of the absorber more difficult. On top of this, on account of the transit times, that are not known a priori, of the pressure waves relative to the measurement surface, the measurement surface has to be observed continuously, i.e. at least having a temporal resolution of the order of magnitude of nanoseconds, during several microseconds. It is not readily obvious how this can be achieved using an electronic camera that is available today.

The object of the invention is to propose a method for photoacoustic tomography that enables faster data acquisition for measuring the deformations of the sample surface than in the prior art.

The object is achieved by a method for photoacoustic tomography of a sample, deformations on a measurement surface of the sample being measured as a function of location and time, the deformations resulting from the absorption of a pulsed excitation radiation on at least one spectrally addressable target structure in the sample interior while emitting thermomechanical pressure waves in the direction of the measurement surface, and the measured deformations being fed to a reconstruction method for determining the position of the target structure in the sample interior, characterized in that
 a. a leading and a trailing observation laser pulse relative to an excitation pulse are irradiated onto the measurement surface,
 b. a two-dimensional deformation profile of the measurement surface being determined from the observation laser pulses scattered by the measurement surface, by means of the method of double-pulse electronic speckle interferometry (ESPI), and
 c. the temporal distance between the excitation pulse and the trailing observation laser pulse being assigned to the predetermined deformation profile as a time index, and
 d. a predetermined number of repetitions of steps a to c taking place by varying at least the temporal distance between excitation pulse and trailing observation laser pulse.

The sub claims specify advantageous designs.

According to the invention, a deformation profile is determined from two subsequently carried-out illuminations of a measurement surface on the sample using observation laser light and related to the temporal distance of a third light pulse, which is applied between the two observation laser pulses, to the latter of the two observation laser pulses.

This third light pulse is to enter into the sample and be absorbed by the target structure. It represents the excitation light of the PAT measurement and originates from a different part range of the electromagnetic spectrum than the observation laser light.

The sequence of the three light pulses is repeated N times (N being a natural number that can be specified in advance) while changing at least the temporal distance that has been mentioned, to generate a sequence of N deformation profiles at N different time indices.

The distance between two subsequent time indices, that has been assigned to the deformation profiles in the sequence generated, is, as a rule, much smaller than the actual time span between the detection of two subsequent deformation profiles by measuring. Nevertheless, the sequence that has been obtained by repetition of three consecutive light pulses approximates a "true sequence of deformation profiles" that occurs within a few microseconds after the excitation pulse on account of only one excitation pulse on the measurement surface. To detect the "true sequence" would, however, presuppose technically that an electronic camera is available that could record several millions of images per second. However, the state of camera technology is at present three orders of magnitude below this. In contrast, the sequence generated according to the invention represents a realizable measurement result and at the same time an adequate starting data set for tomographic reconstruction in the sense of PAT.

An important advantage of the invention relative to the prior art can be seen in the fact that the detection in terms of measurement technology, of all raw data for subsequently calculating the sequence of deformation profiles can be finished without any problems in less than ten seconds, preferably in less than one second, particularly preferably in less than 200 milliseconds.

The invention is explained below in more detail also using figures. In the drawings.

Figure 1:
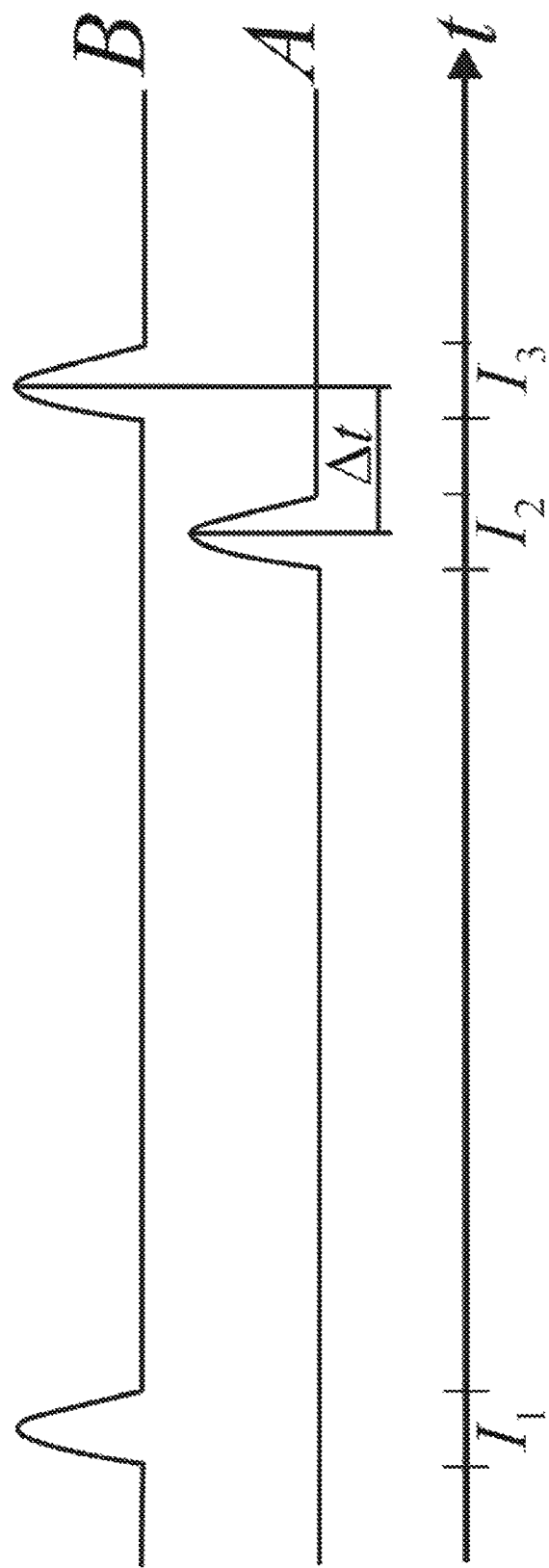
FIG. 1 shows a sketch of the temporal arrangement of two observation laser pulses (B) and of the excitation pulse (A) for determining a deformation profile having the time index $\Delta t$.

To determine a single deformation profile of the measurement surface, three light pulses are irradiated as sketched in FIG. 1. The irradiation of the three light pulses takes place in three, preferably non-overlapping, time intervals ($I_1$, $I_2$, $I_3$) one after the other,
 . . . in a first time interval ($I_1$) the measurement surface being irradiated using observation light from a laser light source;
 . . . in a second time interval ($I_2$) the sample being irradiated using excitation light that can enter into the interior of the sample and be absorbed by the spectrally addressable target structures;
 . . . in a third interval ($I_3$) a further illumination of the measurement surface taking place using observation light from the laser light source.

The center distance between the second and the third time interval is the temporal distance Δt for which a deformation profile is determined. As described in the prior art, the deformation profile is calculated from the detected speckle patterns that are acquired for the observation laser pulses of the first and the third time interval by an electronic camera. The deformation profile then in particular represents the change of the deformation state of the sample surface between the first time interval (prior to the arrival of the excitation pulse) and the third time interval (Δt after the arrival of the excitation pulse).

The observation laser pulse that is irradiated onto the measurement surface during the first time interval is termed the "leading" observation laser pulse. It is followed temporally by the excitation pulse that again is followed in the third time interval by the "trailing" observation laser pulse.

The excitation pulse can be a laser light pulse. It can also originate from another light source that is arranged to emit light pulses at predetermined moments, for example a flash lamp. The pulse duration of the excitation pulse should preferably be smaller than the acoustic transit time of the absorber (conventionally defined as diameter of the absorber divided by the speed of sound in the absorber), in order to maximize the pressure amplitude, and be in the order of magnitude of nanoseconds. The pulse duration is preferably less than 100 ns, particularly preferably less than 10 ns.

According to the invention, the second time interval in which the sample is illuminated using excitation light should be variable between the first and third time interval in terms of its temporal distance from the third time interval. This can be achieved for example by triggering the emission of the excitation pulse by an electronic drive system that is controlled by a control unit (trigger box). Here, the control unit can use the time cycle of an internal clock. It can also receive signals that indicate the emission of an observation laser pulse and use these signals for temporal synchronization. Such signals can originate from the observation laser or from its drive system or also from a photo diode onto which part of the observation laser light is directed.

It is also within the framework of the invention to vary the temporal distance of the first and third time interval, i.e. the leading and trailing observation laser pulse, during the N fold repetition of the sequence of the three laser pulses. Even then, each sequence of light pulses can be assigned a predetermined temporal distance Δt between the excitation pulse and the trailing observation laser pulse, possibly using the synchronization already mentioned.

If the electronic camera records the speckle patterns of the observation laser light pulses across a predetermined number N of repetitions of the pulse sequence, a sequence of deformation profiles can be calculated from the measurement data. Each deformation profile of the sequence is assigned a different temporal distance Δt.

It is a preferred design of the invention to continuously vary the predetermined temporal distance Δt, i.e. either to increase it or to reduce it for each repetition. In this case, this shall be termed the incrementation of the temporal distance, it being possible to vary the absolute value of the increment. However, the increment has no change of sign. Its absolute value is to be in the order of magnitude of nanoseconds and preferably 1-100 ns, particularly preferably 10-50 ns.

A particularly advantageous realization—because simple technically—of the temporal control of the three pulses is achieved in that a repeating, pulsed observation laser having a fixed pulse frequency PB and a likewise repeating, pulsed excitation light source having a fixed pulse frequency PA are used, PA being slightly larger or smaller than PB/2, i.e. $0 < |PA - PB/2| \ll |PA|$. The choice of the difference of PA and PB/2 directly establishes the increment that is now constant. Three light pulses of two observation light pulses each and an excitation pulse are then irradiated onto the sample in a single sequence, the excitation pulse then arriving slightly earlier or later relative to the trailing observation laser pulse for each further repetition of the pulse sequence.

All determined deformations, in their entirety, form a data array that is indexed by a function of location—indexed by pixel coordinates of the camera—and time—indexed by a time index that corresponds to the values of Δt incremented during the course of the sequence. This "film" of the measurement-surface deformation that is available in the form of electronic data is a suitable input variable for a reconstruction routine for localizing the sources of the pressure waves.

A sequence of 100 deformation profiles whose temporal distances are for example incremented by 50 ns each, covers the first 5 μs after the arrival of the excitation pulse. In the case a known speed of sound of the sample of for example 1 km/s, only pressure waves from target structures can then be detected that are less than 5 mm below the surface, even if the excitation light can penetrate more deeply. Recording the data for calculating such a film requires—typically, but not compulsory (see below)—the electronic storage of 200 images of the sample using the observation laser.

The measurement values that have been acquired on the electronic camera, together with in each case the assigned pixel coordinates and the respective temporal distance Δt between the second and third time interval are recorded, stored preferably in an electronic memory for computer-aided post processing and/or written onto a non-volatile electronic memory medium. The post processing for calculating the speckle phases and the temporally resolved deformation of the sample surface can take several minutes, but this post-processing time is of no importance.

What is decisive, is rather the duration of the capture of data (acquisition time below) that, using the invention, can now remain below ten seconds, preferably below one second, particularly preferably even below 200 ms. Using a commercially available camera having a frame rate of e.g. 2000 fps (frames per second), up to 400 images or 200 deformation profiles can be acquired during 200 ms, that then represent a very short time span after the absorption of an excitation pulse, e.g. up to 10 μs.

In the method described so far, each illumination pulse is recorded separately during a camera exposure (i.e. in a time interval having the length of the exposure time of the camera).

By changing the repetition rates of the radiation sources and possibly varying the camera frame rate, the acquisition method can be accelerated or slowed down. The acquisition time (or the sampling rate if the number of repetitions of the pulse sequence is predetermined as N) has to be selected taking into account the proper motion of the sample that has to be expected, and the energy input per unit time into the sample, that takes place as a result of the excitation radiation. For faster samples, the sampling rate should be higher than during samples that are at rest or that move only slowly. However, this also causes more energy per unit time to penetrate into the sample, which can result in thermal damage give a certain excitation energy.

It is possible to shorten the total acquisition time if several individual pulse exposures that are recorded together only during one camera exposure can subsequently be separated computationally. This is achieved if the existence of the temporal distance of the laser pulses can be coded into the camera recording, as the following advantageous development shows:

Into the embodiment of DP ESPI, described by Pedrini et al., having a first fringe pattern on the sensor, preferably a second fringe pattern on the sensor is introduced that runs orthogonally to the first one. For example this is possible by splitting the laser light into a first sample beam and two reference beams before it reaches the sample, each reference beam being guided to the camera across its own reference arm of the interferometer. The reference arms can radiate onto the camera from different angles, in particular in each case at an angle relative to the optical axis of the camera such that phase ramps of the reference light, that mutually run at right angles, are formed along the horizontal and the vertical pixel axis. Interference with the sample beam that enters along the optical axis then generates mutually orthogonal fringe patterns.

If furthermore care is taken that only the first reference arm radiates light onto the camera when the interferogram of the leading observation laser pulse is acquired and only the second one for the trailing pulse, then a camera recording having a complex fringe structure is produced that can subsequently be evaluated line by line and/or column by column, to the determine the phase profiles for both illuminations. In this way, a deformation profile can eventually be determined using only one camera exposure.

Alternative coding of two observation laser pulses in a single camera recording can consist in using the polarization of the observation light. Using a mask on the camera pixels that make each pixel sensitive for only one polarization direction, and for example a "checker board-like" mask structure, both observation laser pulses can be transmitted through a fast switching polarizer and thus be transferred into one each of two orthogonal polarization states. To the extent that the sample largely maintains the polarization during the scattering, the camera records the interferogram of the first pulse on different pixels than that of the second pulse. In the joint image of the camera, both are then to be separated directly by addressing the pixels.

If imaging using a lesser tomographic resolution is desired or is sufficient for the purposes of the user, temporal sampling can take place using a lower sampling rate, leading to fewer repetitions and thus to less irradiated excitation energy per unit time. In particular it can be advantageous to reduce the sampling rate if one is mainly interested in target structures that are localized deeply below the sample surface. The pressure waves originating there exhibit a sound-frequency spectrum and pass a low-pass filter during the propagation to the sample surface on account of a frequency-dependent damping in many sample materials. The deformations of the sample surface by pressure waves that run far can thus be also detected using a reduced temporal resolution which stresses the sample less likewise by fewer excitation pulses per unit time.

Figure 2:
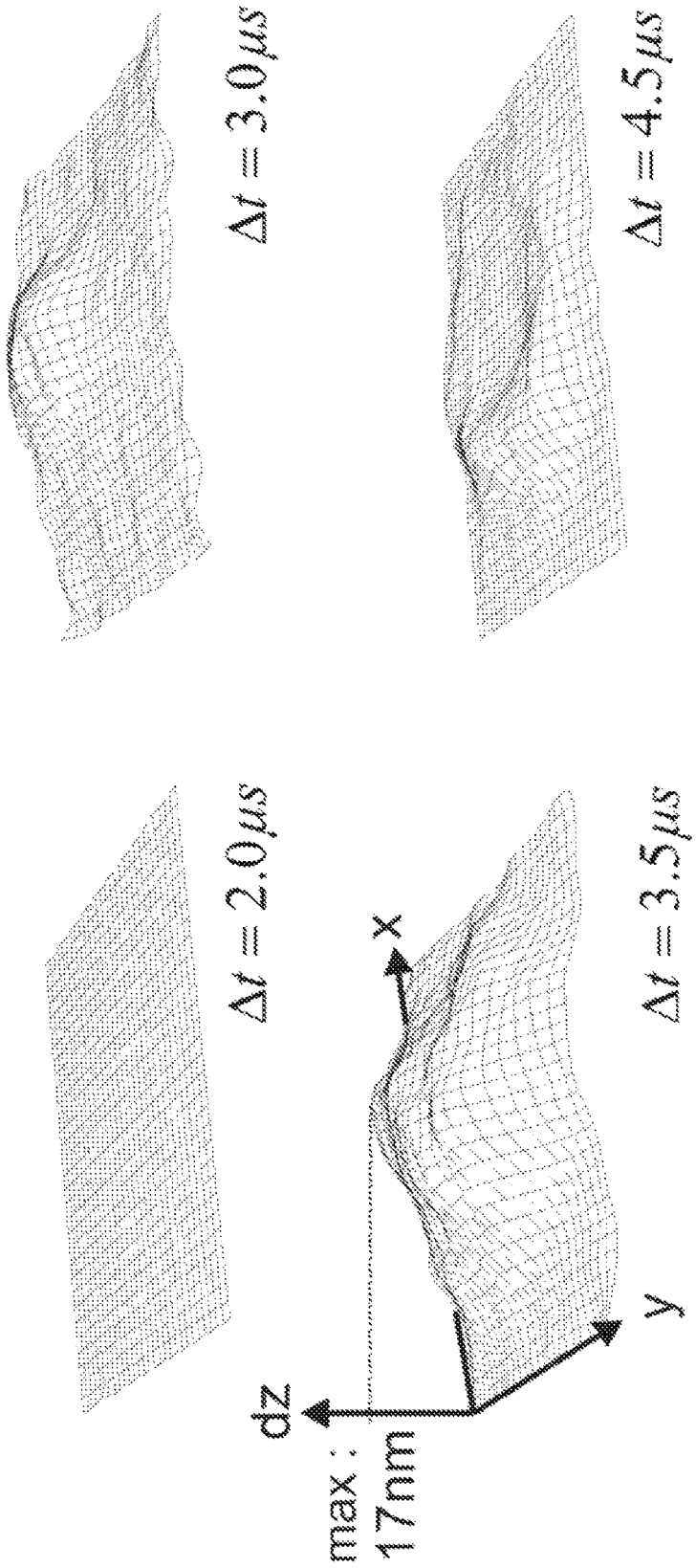
FIG. 2 shows the illustration of four deformation profiles from measurement data on a silicon phantom at four different time indices.

FIG. 2 for example shows deformation profiles on a sample phantom that have been detected according to the invention. The underlying measurement setup in principle corresponds to that of Pedrini et al. into which additionally a pulsed excitation laser is integrated.

To be specific, $\lambda=1064$ nm is selected as the wavelength of the excitation laser having a pulse duration of 20 ns and a pulse energy of approximately 20 mJ. The wavelength 532 nm having the pulse duration 1 ns and the coherence length 3 mm is used as the observation laser light. About one ninth of the intensity of the observation laser is mirrored out as reference beam before the phantom and guided to the camera. The camera exhibits the following ratings: Progressive Scan 1" CCD sensor having 1600×1200 pixels, pixel size 7.4×7.4 $\mu m^2$, maximum frame rate 35 fps. It is to be noted here that this low frame rate is of course only sufficient for a phantom at rest. Unfortunately, at the time of the measurement no faster camera was available. However, the person skilled in the art now recognizes without any problems that the measurement duration that is required as a whole will be shortened corresponding to the increase in the frame rate.

The sample phantom is a cube having an edge length of approximately one centimeter. Here, the matrix material is silicon that is transparent for visible light, in whose interior a spherical light absorber (diameter approximately 2 mm) of black silicon having a high optical absorption is arranged. In addition that side of the cube that is irradiated using the illumination light is coated with a thin layer of white silicon. White silicon exhibits a high optical scattering coefficient. This increases the back scatter and prevents the illumination radiation from penetrating deeply into the matrix material that is transparent in this model.

Samples investigated using PAT often exhibit non-ideal properties for DP ESPI measurement. Since the sample material is to exhibit a high penetration depth for the excitation light, it is not always possible to provide observation laser light that is exclusively scattered on the sample surface (the measurement surface). Rather a limited penetration into a layer, that often is only a few micrometers thick, below the measurement surface has to be expected, from which back scattered light can then reach the detector. It can be advantageous for the DP ESPI measurement to coat the measurement surface with a layer containing scattering particles that mainly promotes the scattering of the observation laser light. Preferably ceramic particles, for example a titanium oxide, are suitable for this purpose.

For measuring the deformation on a cubic silicon phantom, excitation and observation light is irradiated onto different cube sides. The camera faces that cube side that is illumined using observation light and images it. The excitation light is irradiated into one of the neighboring cube sides, that is oriented at right angles to the observation side, and penetrates into the transparent matrix material to the absorber and initiates the emission of pressure waves.

Measurement results of the deformation of the sample phantom at selected moments 2 μs, 3 μs, 3.5 μs and 4.5 μs after the irradiation of excitation light are illustrated in FIG. 2. The absorber sphere in the phantom is arranged at a distance of approximately 3 mm from the cube surface facing the camera. The speed of sound in silicon (approximately 1 km/s) results in the oscillation moment, that is to be expected, of the surface approximately 3 μs after excitation. The first part of the figure shows a flat surface after 2 μs, consequently there are no detectable deformations at this time. After the expected 3 μs, a spherical bulge is formed on the surface which increases after 3.5 μs and seems to collapse 4.5 μs after excitation. The deformations are also determined quantitatively by the invention. The maximum detectable local deflection amounts to 17 nm.

To summarize, the invention adapts the double pulse ESPI that is known per se for use in photoacoustic tomography. This is achieved by adding a third light pulse that serves to excite the sample to pressure oscillations and as such is not detected directly by the camera, whose pre-known time of emission between the two observation laser pulses however defining a time index that can be correctly associated with a deformation profile that can be determined. In this way, a sequence of deformation profiles can be determined that approximates the true deformation of the measurement surface after the application of a single excitation pulse, by repeating the pulse sequences while changing the temporal distance between the excitation pulse and the trailing observation laser pulse.

The invention also permits to detect technically all necessary measurement data for surfaces of the order of magnitude of a square centimeter during the course of a few seconds or even during the course of 200 milliseconds. The detected data then still have to be made available to processing and a PAT reconstruction to infer the position of the target structures and/or to illustrate these. But the data acquisition that is finished fast avoids interference and measurement artifacts, in particular if they would result from proper motions or internal motions of the sample.

To this extent, the invention can be termed as "triple pulse PAT". It represents a very advantageous further development of the known PAT method in that it integrates the use of modern high-speed cameras into the PAT method and thus provides a fundamentally new solution to the presently existing problem of data acquisition that is too slow.

The invention claimed is:

1. A method for photoacoustic tomography of a sample, deformations on the measurement surface of the sample being measured as a function of location and time, the deformations resulting from the absorption of a pulsed excitation radiation on at least one spectrally addressable target structure in the sample interior while emitting thermomechanical pressure waves in the direction of the measurement surface, and the measured deformations being fed to a reconstruction method for determining the position of the target structure in the sample interior, characterized in that
   a. an excitation pulse and a leading and a trailing observation laser pulse relative to the excitation pulse are irradiated onto the measurement surface,
   b. a two-dimensional deformation profile of the measurement surface is determined, using double-pulse electronic speckle interferometry (ESPI), by recording on a two-dimensional light-detector array a first speckle pattern resulting from scattering of the leading observation laser pulse by the measurement surface and a second speckle pattern resulting from scattering of the trailing observation laser pulse by the measurement surface, determining a phase difference of speckles in the first and second speckle patterns, and determining a movement of the measurement surface based on the determined phase difference,
   c. the temporal distance between the excitation pulse and the trailing observation laser pulse is assigned to the two-dimensional deformation profile as a time index, and
   d. a predetermined number of repetitions of steps a to c take place by varying at least the temporal distance between the excitation pulse and the trailing observation laser pulse.

2. The method according to claim 1, wherein the excitation pulses exhibits a pulse durations of at most 100 nanoseconds.

3. The method according to claim 1, wherein the repetitions of steps a to c take place while varying the temporal distance between the leading and the trailing observation laser pulses.

4. The method according to claim 1, wherein the repetitions of steps a to c take place while incrementing the temporal distance between the excitation pulse and the trailing observation laser pulse.

5. The method according to claim 1, wherein the excitation pulse has a pulse rate PA, the observation laser pulse has a pulse rate PB, and the pulse rates PA and PB satisfy the condition $0<|PA-PB/2|<<|PA|$.

6. The method according to claim 4, wherein the absolute value of the increment of the temporal distance between the excitation pulse and the trailing observation pulse is selected from the interval 1-100 nanoseconds.

7. The method according to claim 1, wherein the scattering of the observation laser pulses from the measurement surface is enhanced by applying particles to the measurement surface.

8. The method according to claim 7, wherein the particles are ceramic particles.

9. The method according to claim 1, wherein the steps a to d are carried out in less than ten seconds.

10. The method according to claim 8, wherein the ceramic particles are titanium-oxide particles.

11. The method according to claim 9, wherein the steps a to d are carried out in less than one second.

* * * * *

UNITED STATES PATENT AND TRADEMARK OFFICE
CERTIFICATE OF CORRECTION

PATENT NO. : 9,506,742 B2
APPLICATION NO. : 14/195059
DATED : November 29, 2016
INVENTOR(S) : Jens Horstmann and Ralf Brinkmann It is certified that error appears in the above-identified patent and that said Letters Patent is hereby corrected as shown below:

Claim 2, Column 12, Line 14: REPLACE "pulses exhibits" with "pulse exhibits"

Signed and Sealed this
Seventh Day of February, 2017

Michelle K. Lee
*Director of the United States Patent and Trademark Office*